United States Patent
Wahl

(10) Patent No.: US 11,457,915 B2
(45) Date of Patent: *Oct. 4, 2022

(54) SURGICAL BENDING INSTRUMENT

(71) Applicant: In2Bones USA, LLC, Memphis, TN (US)

(72) Inventor: Rebecca Hawkins Wahl, Escondido, CA (US)

(73) Assignee: In2Bones USA, LLC, Memphis, TN (US)

( * ) Notice: Subject to any disclaimer, the term of this patent is extended or adjusted under 35 U.S.C. 154(b) by 273 days.

This patent is subject to a terminal disclaimer.

(21) Appl. No.: 16/826,539

(22) Filed: Mar. 23, 2020

(65) Prior Publication Data

US 2020/0214701 A1   Jul. 9, 2020

Related U.S. Application Data

(63) Continuation of application No. 16/031,973, filed on Jul. 10, 2018, now Pat. No. 10,610,222, which is a
(Continued)

(51) Int. Cl.
*A61B 17/064* (2006.01)
*A61B 17/068* (2006.01)
(Continued)

(52) U.S. Cl.
CPC ........ *A61B 17/068* (2013.01); *A61B 17/0642* (2013.01); *A61B 17/0682* (2013.01);
(Continued)

(58) Field of Classification Search
CPC ............ A61B 17/0682; A61B 17/0642; A61B 17/068
See application file for complete search history.

(56) References Cited

U.S. PATENT DOCUMENTS

| | | | | |
|---|---|---|---|---|
| 3,960,147 A | * | 6/1976 | Murray | A61B 17/8872 606/101 |
| 4,263,903 A | | 4/1981 | Griggs | |
| 4,592,346 A | * | 6/1986 | Jurgutis | A61B 17/10 411/457 |
| 5,425,490 A | | 6/1995 | Goble et al. | |

(Continued)

FOREIGN PATENT DOCUMENTS

EP     0127994 A1     12/1984

*Primary Examiner* — Christian A Sevilla
(74) *Attorney, Agent, or Firm* — Rutan & Tucker LLP; Hani Z. Sayed

(57) ABSTRACT

An apparatus and a method are provided for a surgical bending instrument for bending surgical implants. The surgical bending instrument comprises a body including a longitudinally extending threaded hole. A shaft comprising a threaded portion is rotatably engaged within the threaded hole. A handle is coupled to a proximal end of the shaft, and a distal extension of the shaft comprises a driver. A distal force applicator comprises the driver centered between a first grip and a second grip. In some embodiments, the distal force applicator is configured to retain a surgical staple, such that the surgical staple may be changed to a distracted configuration suitable for implantation at a bone fixation or fusion site of a patient. In some embodiments, the distal force applicator is configured to bend a bone fusion plate so as to tailor the plate to specific anatomy of the patient's bone.

9 Claims, 9 Drawing Sheets

Related U.S. Application Data continuation of application No. 15/480,612, filed on Apr. 6, 2017, now Pat. No. 10,010,320, and a continuation-in-part of application No. 15/992,065, filed on May 29, 2018, now Pat. No. 10,863,982, and a continuation of application No. 15/041,959, filed on Feb. 11, 2016, now Pat. No. 10,052,103.

(60) Provisional application No. 62/116,387, filed on Feb. 14, 2015.

(51) Int. Cl.
*A61B 17/88* (2006.01)
*A61B 17/072* (2006.01)

(52) U.S. Cl.
CPC ........ *A61B 17/072* (2013.01); *A61B 17/8863* (2013.01); *A61B 2017/0645* (2013.01); *A61B 2017/07235* (2013.01)

(56) References Cited

U.S. PATENT DOCUMENTS

| | | |
|---|---|---|
| 6,533,157 B1 | 3/2003 | Whitman |
| 8,590,760 B2 | 11/2013 | Cummins et al. |
| 2008/0319443 A1 | 12/2008 | Focht et al. |
| 2009/0118734 A1* | 5/2009 | Bhatnagar .......... A61B 17/0642 606/75 |
| 2009/0254090 A1 | 10/2009 | Lizee |
| 2011/0204120 A1 | 8/2011 | Crainich |
| 2013/0153631 A1 | 6/2013 | Vasudevan et al. |
| 2013/0206815 A1* | 8/2013 | Fox .................... A61B 17/0642 227/176.1 |
| 2013/0231667 A1 | 9/2013 | Taylor et al. |
| 2014/0097228 A1* | 4/2014 | Taylor ................... A61B 17/80 227/181.1 |
| 2014/0172024 A1 | 6/2014 | Horwitz |
| 2016/0199060 A1* | 7/2016 | Morgan ................ A61B 17/10 227/175.1 |
| 2016/0338697 A1 | 11/2016 | Biedermann et al. |
| 2017/0303978 A1 | 10/2017 | Palmer et al. |
| 2018/0008263 A1 | 1/2018 | Goldstein et al. |

\* cited by examiner

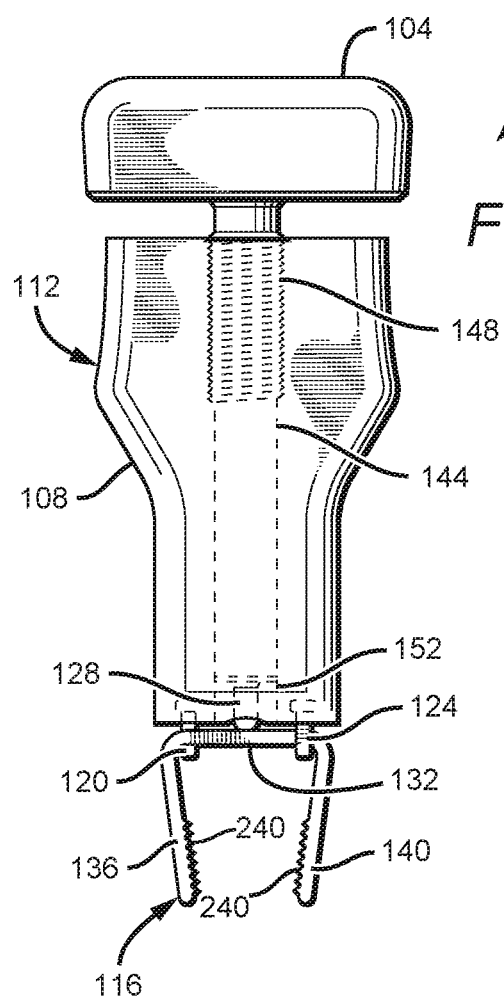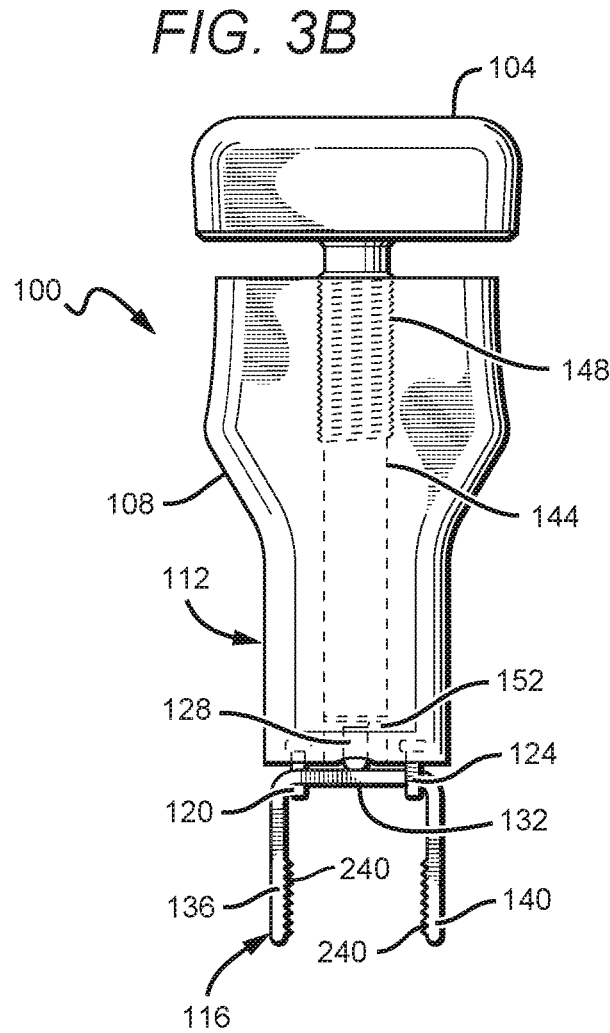

SURGICAL BENDING INSTRUMENT

PRIORITY

This application is a continuation of, and claims the benefit of, U.S. Patent Application, entitled "Surgical Bending instrument," filed on Apr. 6, 2017 and having application Ser. No. 15/480,612, which is a continuation-in-part of, and claims the benefit of, U.S. Patent Application, entitled "Surgical Bending Instrument," filed on May 29, 2018 and having application Ser. No. 15/992,065, which is a continuation of, and claims the benefit of, U.S. Patent Application, entitled "Surgical Bending Instrument," filed on Feb. 11, 2016 and having application Ser. No. 15/041,959, which claims the benefit of, and priority to, U.S. Provisional Application, entitled "Surgical Bending Instrument," filed on Feb. 14, 2015 and having application Ser. No. 62/116,387, the entirety of each of said applications being incorporated herein by reference.

FIELD

The field of the present disclosure generally relates to securing bones together. More particularly, the field of the disclosure relates to an apparatus and a method for a surgical bending instrument for implanting surgical implants at bone fixation or fusion sites of a patient.

BACKGROUND

Surgical staples or a fusion bone plate implant utilized in conjunction with one or more fasteners may be used to generate compression and stability at a bone interface. An implant generally serves to stabilize bones, or bone parts, relative to one another so as to promote bone fusion. In many applications, surgical staples, or bone plates and fasteners are used to fuse bones, or bone parts, of the human body, such as bones in the foot, the ankle, the hand, the wrist, as well as various other portions of the body. Surgical staples are particularly advantageous in the hands and feet due to a low dorsal profile of the staples once they are implanted. Furthermore, during the course of certain medical procedures, a surgeon may immobilize one or more bones or bone fragments by stabilizing the bones together in a configuration which approximates the natural anatomy. To this end, the surgeon may use fasteners to attach the bones to a bone plate implant so as to hold the bones in alignment with one another while they fuse together.

SUMMARY

An apparatus and a method are provided for a surgical bending instrument for bending surgical implants. The surgical bending instrument comprises a body including a longitudinally extending threaded hole. A shaft comprising a threaded portion is rotatably engaged within the threaded hole. A handle is coupled to a proximal end of the shaft, and a distal extension of the shaft comprises a driver. A distal force applicator comprises the driver centered between a first grip and a second grip. In some embodiments, the distal force applicator is configured to retain a surgical staple, such that the surgical staple may be changed to a distracted configuration suitable for implantation at a bone fixation or fusion site of a patient. In some embodiments, the distal force applicator is configured to bend a bone fusion plate so as to tailor the plate to specific anatomy of the patient's bone. The surgical bending instrument may be packaged into sterile surgery-specific kits comprising other surgical tools, such as drill guides, drill sizers, tamps, forceps, staple removal tools, drills, temporary pins, drill depth stops, fusion bone plates, bone plate fasteners, compression screws, and the like.

In an exemplary embodiment, a surgical bending instrument for bending surgical implants comprises a body supporting a distal force applicator and a proximal handle; a first grip and a second grip of the distal forced applicator configured to retain the surgical implant; and a driver of the distal force applicator configured to exert a distally-directed force so as to bend the surgical implant.

In another exemplary embodiment, a shaft is threadably engaged within a longitudinally extending hole within the body, a distal extension of the shaft comprising the driver, and a proximal handle is fixedly coupled to a proximal end of the shaft. In another exemplary embodiment, the driver and the shaft are separate components that are engaged with one another. In another exemplary embodiment, the shaft communicates mechanical forces applied at the proximal handle to the driver. In another exemplary embodiment, rotating the proximal handle relative to the body moves the driver longitudinally relative to the body. In another exemplary embodiment, twisting the proximal handle clockwise moves the driver distally into contact with the crown, such that the surgical staple is clasped between the grips and the driver, wherein further clockwise twisting of the proximal handle changes the surgical staple from an initial configuration to a distracted configuration suitable for implantation across a bone fusion or fixation site of a patient. In another exemplary embodiment, twisting the proximal handle counterclockwise retracts the driver proximally away from the crown, allowing the surgical staple to relax from the distracted configuration and compress the bone fusion or fixation site.

In another exemplary embodiment, a lever comprising a wheel and a peripheral cam is rotatably mounted on a pivot within the body, such that when the lever is moved proximally, the cam forcibly pushes the driver so as to exert a distally-directed force onto the surgical implant. In another exemplary embodiment, a lever comprising a wheel and a peripheral cam is rotatably mounted on a pivot within the body, such that moving the lever proximally causes the cam to exert a distally-directed force onto the surgical implant. In another exemplary embodiment, the surgical bending instrument comprises a rigid material suitable for bending surgical implants.

In another exemplary embodiment, the distal force applicator is configured to retain a surgical staple, such that the surgical staple may be changed to a distracted configuration suitable for implantation at a bone fixation or fusion site of a patient. In another exemplary embodiment, the surgical staple is indicated for fixation of osteotomies and joint arthrodeses of the hands and feet. In another exemplary embodiment, the distal force applicator is configured to bend a bone fusion plate so as to tailor the plate to specific anatomy of a patient's bone.

In another exemplary embodiment, the first and second grips are configured to support a crown of a surgical staple when the driver is placed into forcible contact with the center of the crown. In another exemplary embodiment, the driver and the grips operate to retain the surgical staple within the distal force applicator, thereby facilitating implanting the staple into the patient. In another exemplary embodiment, the first and second grips engage the surgical staple on opposite sides of the crown, thereby preventing the surgical staple from becoming dislodged from the distal force applicator during implantation into a patient. In another exemplary embodiment, the first and second grips have a separation distance comparable with the length of the crown. In another exemplary embodiment, the first and second grips have an adjustable separation distance so as to facilitate using the surgical bending instrument with a variety of differently-sized staples.

In another exemplary embodiment, the surgical bending instrument is packaged into sterile surgery-specific kits comprising other surgical tools, such as drill guides, drill sizers, tamps, forceps, staple removal tools, drills, temporary pins, drill depth stops, fusion bone plates, bone plate fasteners, compression screws, and the like.

In an exemplary embodiment, a method of using a surgical bending instrument for implanting a surgical staple at a bone fixation or fusion site of a patient comprises loading the surgical staple into a distal force applicator of the surgical bending instrument, such that the surgical staple is in contact with a first grip and a second grip; advancing a driver into forcible contact with a crown of the surgical staple, the surgical staple being clasped between the first grip, the second grip, and the driver; distracting the surgical staple, such that a first leg and a second leg of the surgical staple are parallel to one another; inserting the surgical staple through an incision and sliding the first and second legs into parallel holes drilled across a bone fusion or fixation site of the patient; retracting the driver from the crown so as to allow the surgical staple to compress the bone fusion or fixation site; disengaging the first and second grips from the crown; pushing the surgical staple into the parallel holes until the crown is in contact with the patient's bone; and closing the incision by way of suturing.

In another exemplary embodiment, advancing further comprises rotating a proximal handle clockwise so as to move the driver distally into contact with the crown, the driver being connected to the proximal handle by way of a threaded shaft extending longitudinally through the surgical bending instrument. In another exemplary embodiment, distracting the surgical staple further comprises twisting the proximal handle clockwise to move the driver distally into the crown until the first and second legs are parallel with one another. In another exemplary embodiment, retracting further comprises rotating the proximal handle counterclockwise so as to move the driver proximally away from the crown, thereby allowing the first and second legs to bend toward one another.

In an exemplary embodiment, a surgical bending instrument for implanting a surgical staple at a bone fusion site of a patient comprises: a body supporting a first grip and a second grip that are configured to retain a crown of the surgical staple; a driver configured to exert a distally-directed force onto the top of the crown between the first grip and the second grip; and a proximal handle configured to move the driver longitudinally relative to the body.

In another exemplary embodiment, the first grip and the second grip are disposed on the same side of the surgical staple and configured to support opposite ends underneath the crown. In another exemplary embodiment, the first grip and the second grip are configured to forcibly retain the crown when the driver contacts the center of the crown. In another exemplary embodiment, the first grip and the second grip have a separation distance comparable with the length of the crown. In another exemplary embodiment, the first grip and the second grip have an adjustable separation distance so as to facilitate retaining a variety of differently-sized surgical staples.

In another exemplary embodiment, a shaft extending from the proximal handle to the driver is threadably engaged within the body, such that rotating the proximal handle moves the driver relative to the body. In another exemplary embodiment, clockwise rotation of the proximal handle moves the driver distally and clasps the crown between the first grip, the second grip, and the driver, such that further clockwise rotation places the surgical staple into a distracted configuration suitable for implantation across the bone fusion site. In another exemplary embodiment, counterclockwise rotation of the proximal handle moves the driver proximally, allowing the surgical staple to relax from the distracted configuration and compress the bone fusion site.

In another exemplary embodiment, the proximal handle comprises a lever coupled with a cam that is pivotally mounted within the body, such that proximal movement of the lever causes the cam to push the driver into forcible contact with the crown. In another exemplary embodiment, moving the lever to a maximally proximal position places the surgical staple into a distracted configuration suitable for implantation across the bone fusion site. In another exemplary embodiment, moving the lever distally allows the surgical staple to relax from the distracted configuration and compress the bone fusion site.

In an exemplary embodiment, a surgical bending instrument for distracting a surgical staple for implantation at a bone fusion site of a patient comprises: a first grip and a second grip that are disposed on the same side of the surgical staple and configured to support opposite ends underneath a crown of the surgical staple; a driver in mechanical communication with a proximal handle and configured to exert a distal force on top of the crown; and a body supporting at least the first grip, the second grip, and the driver.

In another exemplary embodiment, the proximal handle is configured to facilitate moving the driver distally to clasp the crown between the first grip, the second grip, and the driver, and thereby place the surgical staple into a distracted configuration suitable for implantation across the bone fusion site, and wherein the proximal handle is configured to move the driver proximally to allow the surgical staple to relax from the distracted configuration and compress the bone fusion site after implantation. In another exemplary embodiment, the proximal handle is coupled with the driver by way of a shaft threadably retained within the body, whereby rotating the proximal handle moves the driver longitudinally with respect to the body. In another exemplary embodiment, the proximal handle is coupled with the driver by way of a cam that is mounted pivotally within the body, whereby moving a lever coupled with the cam moves the driver longitudinally relative to the body.

In an exemplary embodiment, a surgical staple for fixating osteotomies and joint arthrodeses comprises a crown comprising an elongate member having a first end and a second end; a first leg coupled with the first end and extending obliquely from the crown toward a centerline of the crown; a second leg coupled with the second end and extending obliquely from the crown toward the centerline of the crown, the first leg and the second leg extending toward one another and sharing an acute angle; and a plurality of teeth disposed on an inner side of the first leg and an inner side the second leg, the plurality of teeth being configured to engage with a bone.

In another exemplary embodiment, the surgical staple is comprised of a material that is amenable to being placed into a distracted configuration and relaxed therefrom, such as by way of a suitable surgical bending instrument. In another exemplary embodiment, the material is comprised of a metal alloy that exhibits shape memory and superelastic properties, such as Nitinol or other similar material.

In another exemplary embodiment, the plurality of teeth are biased toward the crown, such that the plurality of teeth offer relatively little resistance during implantation of the surgical staple into the bone and fixate the surgical staple within the bone after implantation. In another exemplary embodiment, the plurality of teeth is comprised of seven teeth disposed along each of the first leg and the second leg. In another exemplary embodiment, one or more exterior teeth are disposed along each of the first leg and the second leg, the one or more exterior teeth being configured to cooperate with the plurality of teeth to engage the bone and prevent movement of the surgical staple after being implanted into the bone. In another exemplary embodiment, one or more teeth are disposed along the crown and configured to engage with bone and prevent lateral movement of the crown along the surface of the bone. In another exemplary embodiment, the one or more teeth are biased toward a centerline of the crown.

In another exemplary embodiment, the crown further comprises an upper reinforced portion and a valley underneath the reinforced portion, the valley being centrally disposed along the lower surface of the crown and bordered by edges. In another exemplary embodiment, the edges are configured to engage with bone and prevent lateral movement of the crown along the surface of the bone once the surgical staple is implanted. In another exemplary embodiment, the reinforced portion is configured to impart structural integrity to the surgical staple in compensation for the presence of the valley.

In another exemplary embodiment, the crown is comprised of wing portions disposed at opposite ends of the crown and extending beyond the first leg and the second leg. In another exemplary embodiment, the wing portions are configured to cooperate with at least the plurality of teeth to fixate the surgical staple once implanted in the bone. In another exemplary embodiment, the wing portions are configured to receive grips of a surgical bending instrument that is configured to place the surgical staple into a distracted configuration.

In an exemplary embodiment, a surgical staple for fixating osteotomies and joint arthrodeses comprises a crown comprised of an elongate member having a first end and a second end; a first transverse portion disposed at the first end; a second transverse portion disposed at the second end; a first leg and a second leg extending downward and parallelly from opposite ends of the first transverse portion; a third leg and a fourth leg extending downward and parallelly from opposing ends of the second transverse portion; and a plurality of teeth disposed on each of the first leg, the second leg, the third leg, and the fourth leg and oriented toward a centerline of the crown.

In another exemplary embodiment, the first leg and the third leg extend obliquely from the crown toward the centerline and share an intervening acute angle, and wherein the second leg and the fourth leg extend obliquely from the crown toward the centerline and share an intervening acute angle. In another exemplary embodiment, the plurality of teeth disposed on the first leg and the plurality of teeth disposed on the third leg are oriented toward one another and biased toward the crown, such that the first leg and the third leg cooperate to engage with a bone disposed therebetween. In another exemplary embodiment, the plurality of teeth disposed on the second leg and the plurality of teeth disposed on the fourth leg are oriented toward one another and biased toward the crown, such that the second leg and the fourth leg cooperate to engage with a bone disposed therebetween.

In another exemplary embodiment, one or more exterior teeth are disposed along at least one of the first leg, the second leg, the third leg, and the fourth leg, the one or more exterior teeth being configured to cooperate with the plurality of teeth to engage a bone and prevent movement of the surgical staple after being implanted into the bone. In another exemplary embodiment, wing portions are disposed at opposite ends of the crown and extending beyond the first transverse portion and the second transverse portion. In another exemplary embodiment, the wing portions are configured to receive grips of a surgical bending instrument that is configured to place the surgical staple into a distracted configuration.

In an exemplary embodiment, a surgical bending instrument for distracting and implanting a surgical staple at a bone fusion site of a patient comprises a body supporting a first grip and a second grip that are configured to retain a crown of the surgical staple; a driver configured to exert a distally-directed force onto the top of the crown between the first grip and the second grip; a proximal handle configured to move the driver longitudinally relative to the body; a size indicator configured to display at least one size of the surgical staple; and a direction indicator configured to display a direction to insert the surgical staple into the first grip and the second grip.

In another exemplary embodiment, the surgical staple is configured for fixating osteotomies and joint arthrodeses of the hands and feet. In another exemplary embodiment, the first grip and the second grip are configured to engage the crown on the same side of the surgical staple. In another exemplary embodiment, the size indicator is embossed, engraved, printed, or otherwise disposed on the surgical bending instrument so as to be directly visible to a practitioner. In another exemplary embodiment, the direction indicator is embossed, engraved, printed, or otherwise disposed on the surgical bending instrument so as to be directly visible to a practitioner.

In another exemplary embodiment, the surgical staple is comprised of a material that is amenable to being placed into a distracted configuration and relaxed therefrom, the surgical staple comprising: an elongate member comprising the crown and having a first end and a second end; a first leg coupled with the first end and extending obliquely from the crown; a second leg coupled with the second end and extending obliquely from the crown, the first leg and the second leg extending toward one another and sharing an acute angle; and a plurality of teeth disposed on the first leg and the second leg, the plurality of teeth being configured to engage with a bone. In another exemplary embodiment, the first grip and the second grip are configured to engage with the first end and the second end of the crown, the crown being comprised of an upper reinforced portion and a valley underneath the reinforced portion, and the valley being centrally disposed along the lower surface of the crown and bordered by edges, the crown being configured to receive the first grip and the second grip so as to place the surgical staple into the distracted configuration. In another exemplary embodiment, the first grip and the second grip are configured to engage with wing portions disposed at opposite ends of the crown and extending beyond the first leg and the second leg, the wing portions being configured to cooperate with at least the plurality of teeth to fixate the surgical staple once implanted in the bone, the wing portions being configured to receive the first grip and the second grip so as to place the surgical staple into the distracted configuration.

In another exemplary embodiment, the surgical staple is configured for fixating osteotomies and joint arthrodeses, the surgical staple comprising: an elongate member comprising the crown and having a first end and a second end; a first transverse portion disposed at the first end; a second transverse portion disposed at the second end; a first leg and a second leg extending downward and parallelly from opposite ends of the first transverse portion; a third leg and a fourth leg extending downward and parallelly from opposing ends of the second transverse portion; and a plurality of teeth disposed on each of the first leg, the second leg, the third leg, and the fourth leg and oriented toward a centerline of the crown. In another exemplary embodiment, the first grip and the second grip share a separation distance comparable with the length of the crown. In another exemplary embodiment, the first grip is configured to engage the crown adjacent to the first transverse portion, and the second grip is configured to engage the crown adjacent to the second transverse portion. In another exemplary embodiment, the first grip and the second grip are configured to engage wing portions disposed at opposite ends of the crown and extending beyond the first transverse portion and the second transverse portion, the wing portions being configured to receive the first grip and the second grip so as to place the surgical staple into a distracted configuration.

BRIEF DESCRIPTION OF THE DRAWINGS

The drawings refer to embodiments of the present disclosure in which:

FIG. 3A illustrates a ghost view of an exemplary embodiment of a surgical bending instrument retaining a surgical staple in an initial configuration, according to the present disclosure;

FIG. 3B illustrates a ghost view of the exemplary embodiment of the surgical bending instrument illustrated in FIG. 3A distracting the surgical staple in accordance with the present disclosure;

Figure 1:
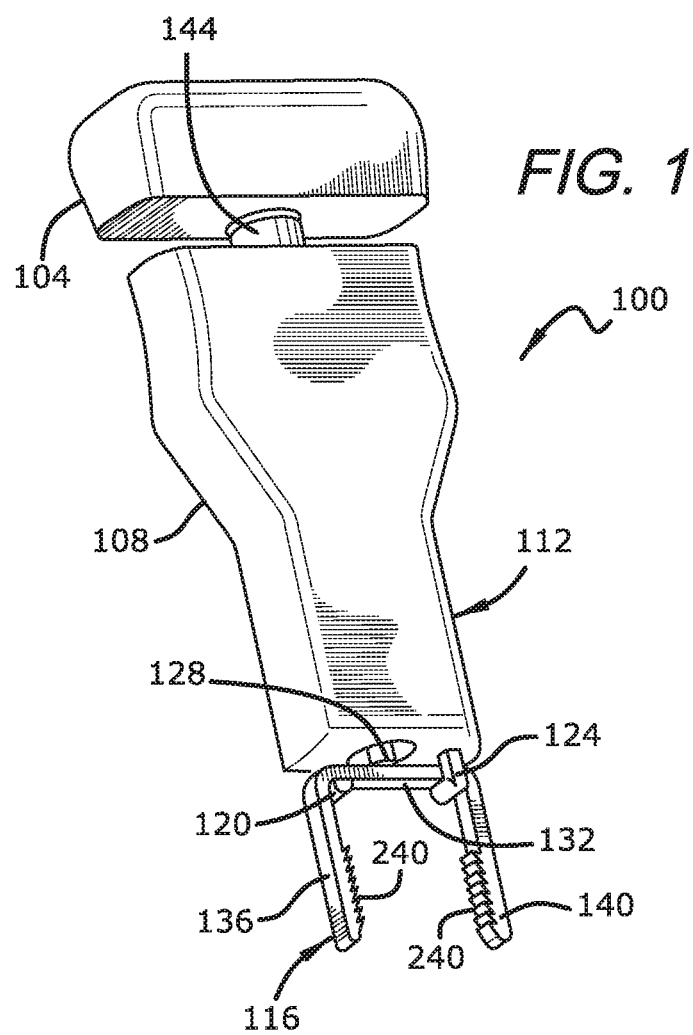
FIG. 1 illustrates an upper perspective view of an exemplary embodiment of a surgical bending instrument in accordance with the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first implant," may be made. However, the specific numeric reference should not be interpreted as a literal sequential order but rather interpreted that the "first implant" is different than a "second implant." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

In general, the present disclosure describes an apparatus and a method for a surgical bending instrument for bending surgical implants. The surgical bending instrument comprises a body including a longitudinally extending hole, at least of portion of which comprising threads. A shaft comprising a threaded portion passes through hole and is rotatably engaged with the threads in the hole. A handle is fixedly coupled to a proximal end of the shaft, and a distal extension of the shaft comprises a driver. A distal force applicator comprises a first grip, a second grip, and the driver centered between the first and second grips. In some embodiments, the distal force applicator is configured to retain a surgical staple, such that the surgical staple may be changed to a distracted configuration suitable for implantation at a bone fixation or fusion site of a patient. In some embodiments, the distal force applicator is configured to bend a bone fusion plate so as to tailor the plate to specific anatomy of the patient's bone.

FIG. 1 illustrates a perspective view of an exemplary embodiment of a surgical bending instrument 100 in accordance with the present disclosure. The surgical bending instrument 100 comprises a proximal handle 104, a body 108, and a distal force applicator 112. In the embodiment illustrated in FIGS. 1-2, a surgical staple 116 is shown loaded within the distal force applicator 112, such that the surgical staple 116 is in a distracted configuration suitable for implantation at a bone fixation or fusion site of a patient. The surgical staple 116 generally is of the variety indicated for fixation of osteotomies and joint arthrodeses of the hands and feet. As such, the surgical staple 116 preferably is comprised of a metal alloy exhibiting shape memory and superelastic properties, such as Nitinol or other similar material. It should be understood, however, that the surgical bending instrument 100 is not to be limited to distracting surgical staples, but rather may be used in various other capacities, such as by way of non-limiting example, bending a bone fusion plate so as to tailor the plate to specific anatomy of a patient's bone being treated.

Figure 2:
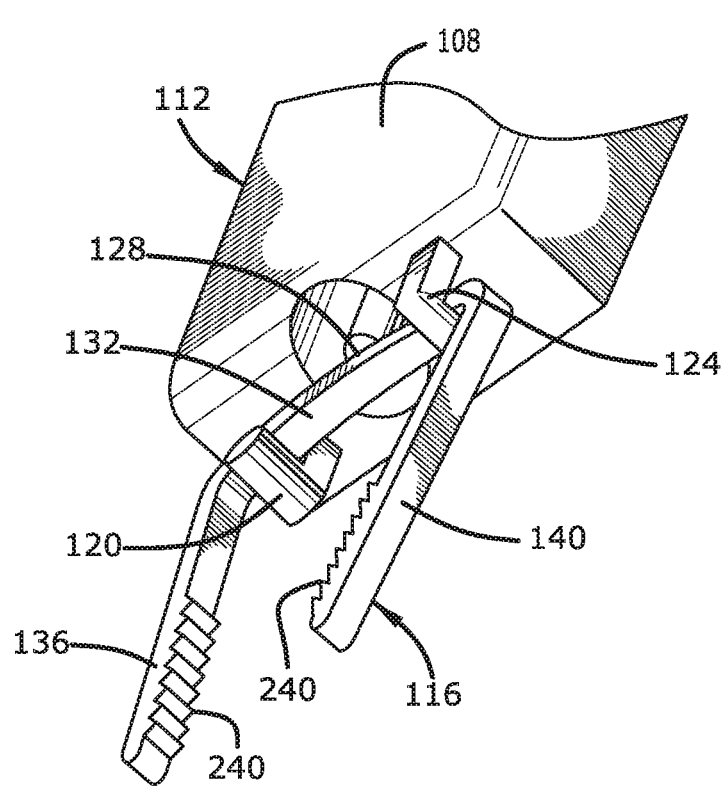
FIG. 2 illustrates a lower perspective view of an exemplary embodiment of a distal force applicator, according to the present disclosure.

As best illustrated in FIG. 2, the distal force applicator 112 comprises a first grip 120, a second grip 124, and a driver 128 centered there between. The first and second grips 120, 124 are configured to cooperate so as to support a crown 132 of the surgical staple 116 when the driver 128 is placed into forcible contact with the center of the crown 132. The forces on the crown 132 due to the driver 128 and the grips 120, 124 operate to retain the surgical staple 116 within the distal force applicator 112, thereby facilitating implanting the staple into the patient. As shown in FIG. 2, the first and second grips 120, 124 are configured to engage the surgical staple 116 on opposite sides of the crown 132. As will be appreciated, engaging the crown 132 on opposite sides advantageously prevents the staple from becoming dislodged from the distal forced applicator 112 during distracting the staple or implantation into the patient.

Preferably, the first and second grips 120, 124 have a separation distance comparable with the length of the crown 132. Thus, as illustrated in FIGS. 3A-3B, the first grip 120 is positioned near a first leg 136 of the surgical staple 132, and the second grip 124 is positioned near a second leg 140 of the staple. It will be appreciated, therefore, that the distal force applicator 112 of the surgical bending instrument 100 is configured to be used with specific sizes of surgical staples 116. In some embodiments, the surgical bending instrument 100 may be configured with an overall size so as to be used with specific sizes of surgical staples 116. In some embodiments, a color-matching system may be utilized to indicate to the surgeon that certain surgical staples 116 may be implanted by way of the surgical bending instrument 100. Further, in some embodiments, the first and second grips 120, 124 may have an adjustable separation distance so as to facilitate using the surgical bending instrument 100 with a variety of differently-sized staples.

FIGS. 3A and 3B illustrate ghost views of the exemplary embodiment of the surgical bending instrument 100 illustrated in FIGS. 1-2. A shaft 144 passing through the body 108 comprises a threaded portion 148 and the above-mentioned driver 128. In the illustrated embodiment, the driver 128 comprises a distal extension of the shaft 144, having a narrower diameter than proximal portions of the shaft 144. In some embodiments, however, the driver 128 and the shaft 144 are separate components which are engaged with one another. It will be appreciated that the shaft 144 communicates mechanical forces applied at the proximal handle 104 to the driver 128, and thus to the crown 132 of the staple. In the illustrated embodiment, the threaded portion 148 is rotatably engaged with similar threads within a hole 152 extending longitudinally through the body 108. The shaft 144 is fixedly coupled with the proximal handle 104 such that rotating the proximal handle 104 relative to the body 108 rotates the shaft 144 within the hole 152, and thus moves the driver 128 longitudinally relative to the body 108.

As best illustrated in FIG. 3A, when the driver 128 is not in contact with the crown, the surgical staple 116 is in an initial configuration wherein the first leg 136 and the second leg 140 of the staple bend toward one another. During operation of the surgical bending instrument 100, twisting the proximal handle 104 clockwise, as viewed from the perspective of a surgeon operating the instrument 100, advances the shaft 144 and moves the driver 128 distally toward the crown 132. Once the driver 128 contacts the center of the crown 132, the surgical staple 116 becomes clasped between the grips 120, 124 and the driver 128. Further clockwise twisting of the proximal handle 104 exerts an increasing degree of force onto the crown 132 by the grips 120, 124 and the driver 128. As will be appreciated, the distally-directed force due to the driver 128 and proximally-directed forces due to the grips 120, 124 cause a corresponding distraction of the first and second legs 136, 140. Thus, clockwise twisting of the proximal handle 104 enables the surgeon to change the surgical staple 116 from the initial configuration, shown in FIG. 3A, to a distracted configuration wherein the first and second legs 136, 140 are forced into a parallel relationship, as illustrated in FIG. 3B.

Once the surgical staple 116 is in the distracted configuration, the surgeon may use the surgical bending instrument 100 to slide the first and second legs 136, 140 into parallel holes drilled across a bone fusion or fixation site of a patient. It will be appreciated that the threaded portion 148 keeps the driver 128 in contact with the crown 132, thereby maintaining the distracted configuration of the surgical staple 116 during implantation. The surgeon may insert the first and second legs 136, 140 into the parallel holes until the first and second grips 120, 124 come into contact with the patient's bone. The surgeon may then twist the proximal handle 104 counterclockwise so as to retract the driver 128 proximally away from the crown 132, thereby allowing the surgical staple 116 to relax from the distracted configuration. The shape memory and superelastic properties of the material comprising the surgical staple 116 ensure that the staple advantageously compresses the bones to be fused as the staple attempts to return to the initial configuration illustrated in FIG. 3A. Once the driver 128 has been suitably retracted from the crown 132, the surgeon may disengage the first and second grips 120, 124 from the crown and then use a tamp to push the legs 136, 140 into the parallel holes until the crown 132 is in direct contact with the bone. The surgeon may then close the incision by way of suturing.

As will be recognized, some surgical procedures may necessitate removing a surgical staple, such as the surgical staple 116, from a bone fusion or fixation site of a patent. It is envisioned that the surgeon may lift the crown 132 away from the patient's bone surface by way of a suitable removal tool so as to create enough clearance for the surgeon to engage the grips 120, 124 between the bone and the crown 132. With the first and second grips 120, 124 suitably engaged with the crown 132, the surgeon may turn the proximal handle 104 clockwise to distally advance the driver 128 into contact with the center of the crown 132. Upon twisting the proximal handle 104 so as to place the surgical staple 116 into the distracted configuration illustrated in FIG. 3A, the surgeon may use the surgical bending instrument 100 to pull the first and second legs 136, 140 free of the patient's bone.

Figure 4A:
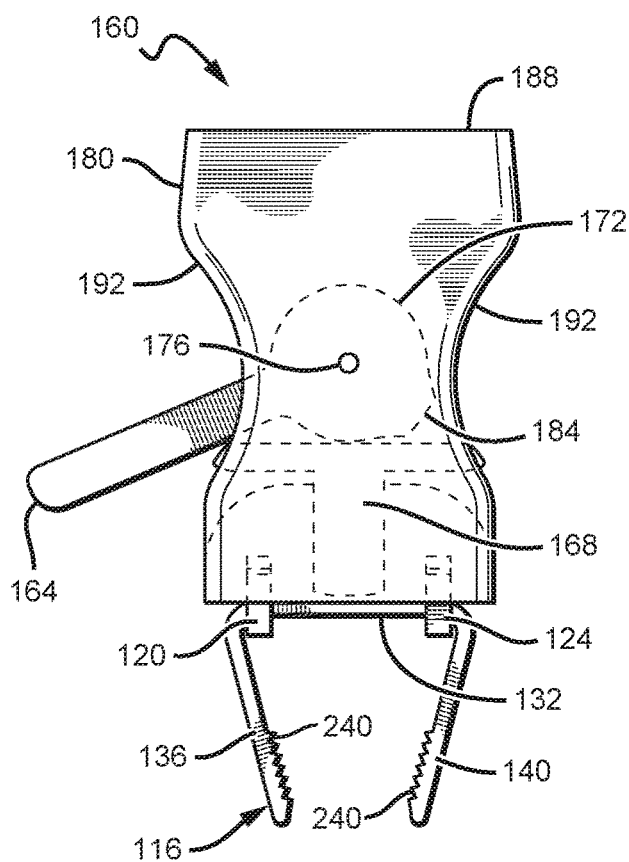
FIG. 4A illustrates a ghost view of an exemplary embodiment of a surgical bending instrument retaining a surgical staple in an initial configuration, according to the present disclosure.
Figure 4B:
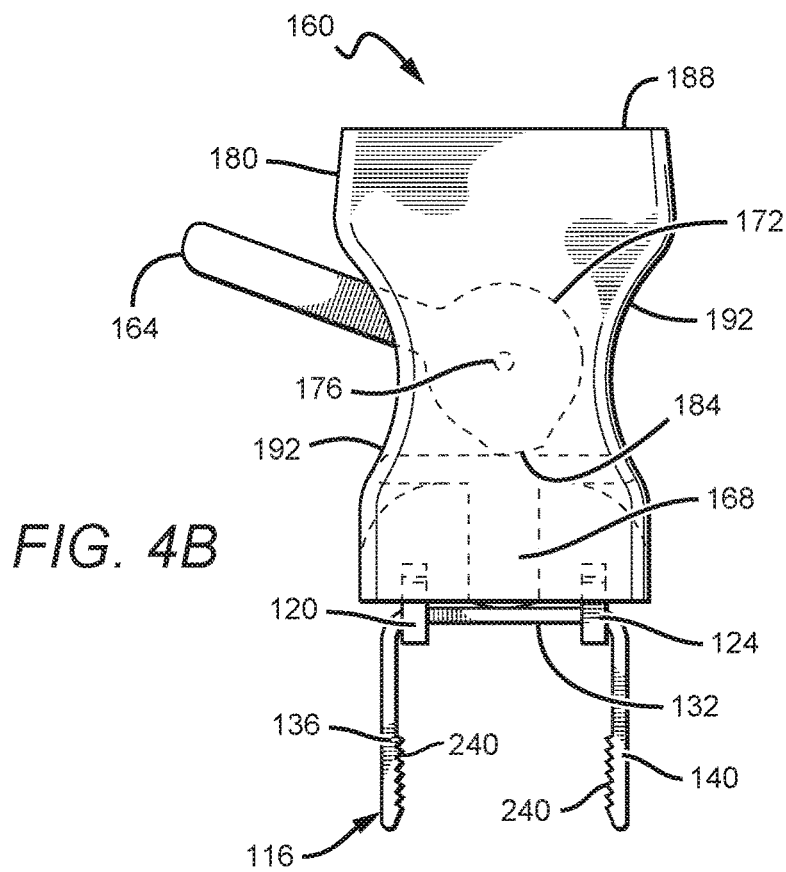
FIG. 4B illustrates a ghost view of the exemplary embodiment of the surgical bending instrument illustrated in FIG. 4A distracting the surgical staple in accordance with the present disclosure.

FIGS. 4A and 4B illustrate ghost views of an exemplary embodiment of a surgical bending instrument 160 retaining the surgical staple 116 in accordance with the present disclosure. The surgical bending instrument 160 illustrated in FIGS. 4A-4B is similar to the surgical bending instrument 100 illustrated in FIGS. 1-2, with the exception that the surgical bending instrument 160 comprises a side lever 164 coupled with a driver 168. The side lever 164 comprises a wheel 172 which is rotatably mounted on a pivot 176 within a body 180 of the surgical bending instrument 160. The wheel 172 is in sliding contact with a proximal portion of the driver 168, such that the side lever 164 may be rotated from a distal position, illustrated in FIG. 4A, to a proximal position as shown in FIG. 4B. The wheel 172 further comprises a cam 184 configured to push the driver 168 distally within the body 180 into the crown 132 when the side lever 164 is rotated to the proximal position. As will be appreciated, the cam 184 and the driver 168 exert a distally-directed force onto the crown 132, thereby distracting the surgical staple 116, as illustrated in FIG. 4B and described herein with respect to FIGS. 3A and 3B.

It will be appreciated that moving the side lever 164 to distract the surgical staple 116 requires a degree of force to be placed onto the lever. A proximal surface 188 of the body 180 advantageously facilitates grasping and stabilizing the surgical bending instrument 160 while the side lever 164 is moved during distraction of the surgical staple 116. A narrow midsection 192 of the body 180 further enables grasping and stabilizing the surgical bending instrument 160 during distraction of the staple 116.

Figure 5A:
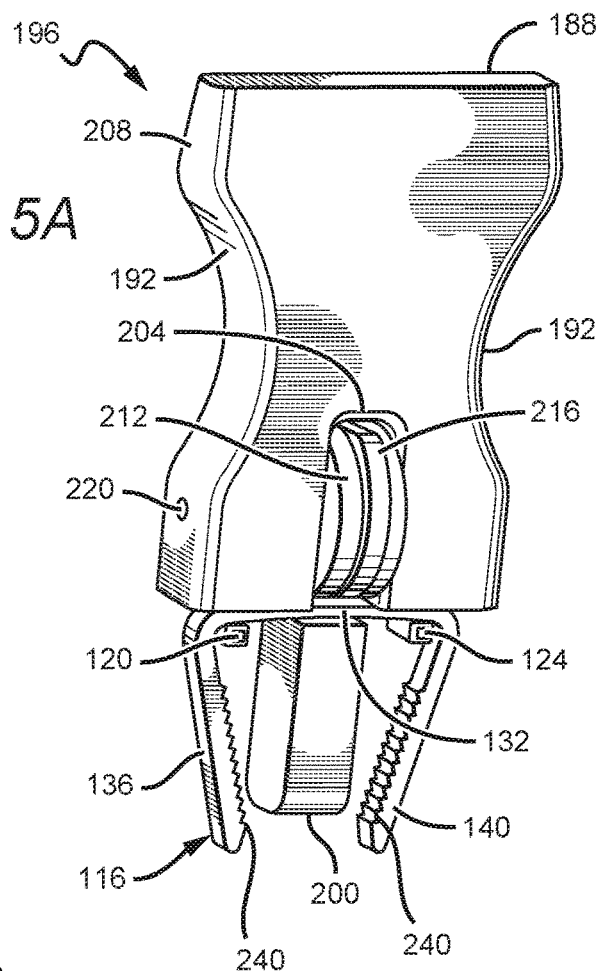
FIG. 5A illustrates an upper perspective view of an exemplary embodiment of a surgical bending instrument retaining a surgical staple in an initial configuration in accordance with the present disclosure.
Figure 5B:
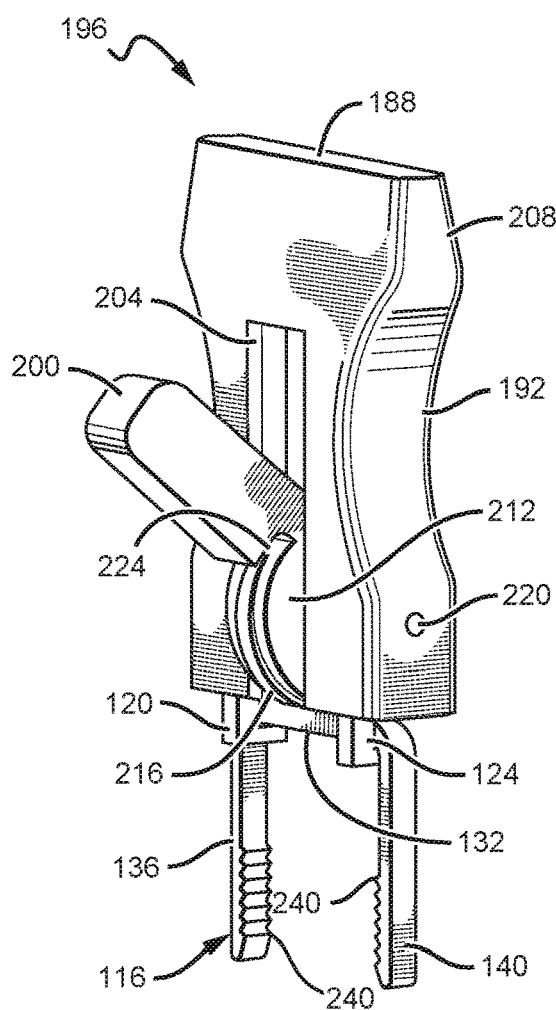
FIG. 5B illustrates an upper perspective view of the exemplary embodiment of the surgical bending instrument illustrated in FIG. 5A distracting the surgical staple in accordance with the present disclosure.

FIGS. 5A and 5B illustrate proximal views of an exemplary embodiment of a surgical bending instrument 196 retaining the surgical staple 116 in accordance with the present disclosure. The surgical bending instrument 196 illustrated in FIGS. 5A and 5B is similar to the surgical bending instrument 160 illustrated in FIGS. 4A-4B, with the exception that the instrument 196 comprises a center lever 200 rotatably positioned within an opening 204 of a body 208. As best illustrated in FIG. 5A, the center lever 200 comprises a wheel 212 and a cam 216 positioned on a periphery of the wheel. The wheel 212 is rotatably mounted on a pivot 220 within the body 208. Unlike previously described embodiments, in the embodiment of FIGS. 5A-5B, the wheel 212 is in direct contact with the crown 132, in absence of a separately, coupled driver. In the embodiment illustrated in FIGS. 5A-5B, the cam 216 operates substantially similarly to the driver described herein. It will be appreciated that the cam 216 is positioned on the wheel 212 so as to exert a distally-directed force on the crown 132 when the center lever 200 is moved from a distal position, illustrated in FIG. 5A, to a proximal position shown in FIG. 5B. As described herein, the distally-directed force on the crown 132 distracts the surgical staple 116 such that the staple may be implanted in the bone of the patent.

As best illustrated in FIG. 5B, the center lever 200 further comprises a slot 224 adjacent to the wheel 212. It will be appreciated that the slot 224 advantageously allows the center lever 200 to be placed into the distal position while the surgical staple 116 is clasped in the first and second grips 120, 124. In some embodiments, the slot 224 is configured to cooperate with the first and second grips 120, 124 so as to retain the surgical staple 116 in the surgical bending instrument while the staple is in the initial configuration, as shown in FIG. 5A.

It should be understood that although embodiments of the surgical bending instrument have been discussed in combination with the surgical staple 116, the surgical bending instruments 100, 160, 196 are not to be limited to distracting surgical staples. Rather, the surgical bending instruments 100, 160, 196 may be used in various capacities other than as described herein, such as by way of non-limiting example, bending a bone fusion plate so as to tailor the plate to a specific anatomy of a patient's bone being treated. Accordingly, it is envisioned that the surgical bending instruments 100, 160, 196 may be packaged into sterile surgery-specific kits comprising other surgical tools and components, such as by way of non-limiting example, drill guides, drill sizers, tamps, forceps, staple removal tools, drills, temporary pins, drill depth stops, fusion bone plates, bone plate fasteners, compression screws, and the like. Further, the surgical bending instruments 100, 160, 196 preferably comprise a rigid material suitable for bending surgical implants, such as surgical staples and bone fusion plates, as described herein. In some embodiments, the surgical bending instruments 100, 160, 196 comprise metal, plastic, or a combination of the two.

Embodiments of the surgical bending instruments 100, 160, 196 have been described in combination with the surgical staple 116. It is to be understood, however, that the surgical staple 116 is not to be limited to the particular embodiment of the surgical staple described in connection with FIGS. 1-5B. As such, it is contemplated that in some embodiments, multiple teeth suitable for engaging with bone may be disposed on one or more surfaces of the surgical staple 116, such as, for example, along a backspan or crown of the staple. In the embodiment of the surgical staple 116, for example, a multiplicity of teeth 240 are disposed along an inner side of each of the legs 136, 140 of the surgical staple 116 so as to discourage movement of the staple once implanted in bone. The teeth 240 may be biased toward the crown 132 so as to facilitate inserting the staple into bone, while discouraging the staple from backing out of the bone after implantation.

Figure 6:
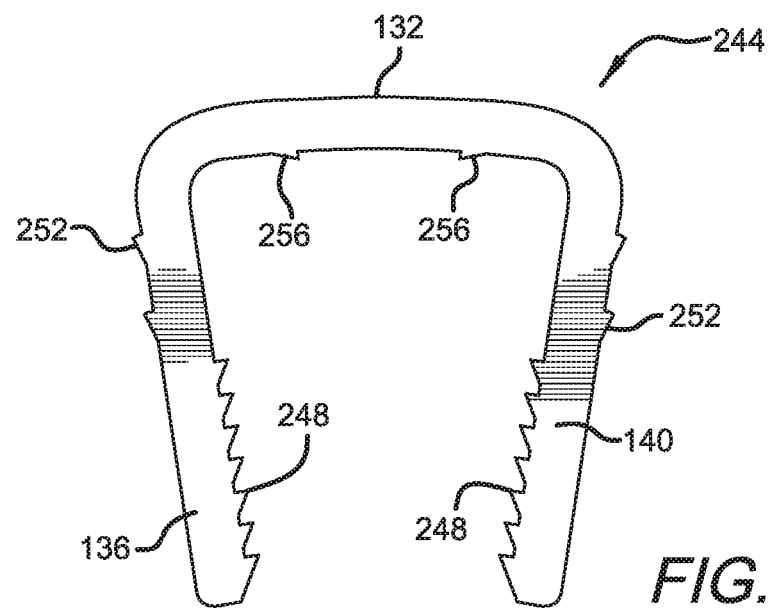
FIG. 6 illustrates a side plan view of an exemplary embodiment of a surgical staple that may be implanted into bone in accordance with the present disclosure.

FIG. 6 illustrates a side plan view of an exemplary embodiment of a surgical staple 244 that may be implanted into bone in accordance with the present disclosure. The surgical staple 244 is similar to the surgical staple 116, and thus the surgical staple 244 generally is of the variety indicated for fixation of osteotomies and joint arthrodeses of the hands and feet. In some embodiments, the surgical staple 244 may be comprised of a material that is amenable to being placed into the distracted configuration and relaxed therefrom, such as by way of any of the surgical bending instruments 100, 160, 196. To this end, the surgical staple 244 may be comprised of a metal alloy that exhibits shape memory and superelastic properties, such as Nitinol or other similar material.

As shown in FIG. 6, multiple teeth 248 are disposed along an inner side of the first and second legs 136, 140. The teeth 248 are biased toward the crown 132, such that the teeth 248 engage with bone and prevent the staple from backing out of the bone after implantation, yet the teeth 248 offer relatively little resistance during implantation of the surgical staple 244 into the bone. Although seven of the teeth 248 are shown disposed along each of the legs 136, 140, it is contemplated that more or less than seven teeth 248 may be incorporated along the legs 136, 140 in various other embodiments of the surgical staple 244. In addition to the teeth 248, multiple exterior teeth 252 may be disposed along the first and second legs 136, 140. As shown in FIG. 6, the surgical staple 244 includes two exterior teeth 252 disposed on an outside of each of the legs 136, 140, near the crown 132. The exterior teeth 252 cooperate with the teeth 248 to engage the bone and prevent movement of the surgical staple 244 after being implanted into the bone.

Figure 7:
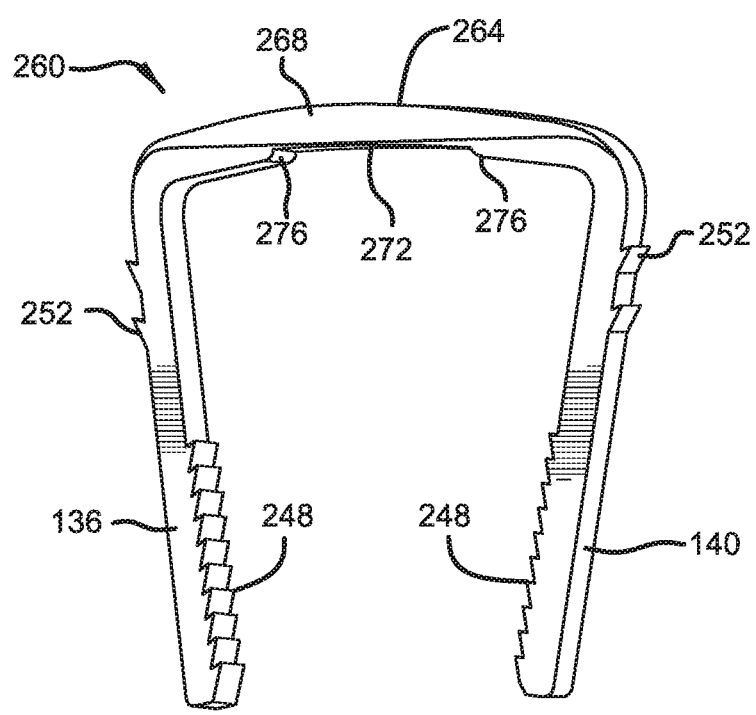
FIG. 7 illustrates a perspective view of an exemplary embodiment of a surgical staple comprised of a crown that includes an upper reinforced portion and a valley underneath the reinforced portion.

Moreover, teeth similar to the teeth 248, 252 are not limited to being disposed along the first and second legs 136, 140, but rather teeth, as well as various other advantageous structures, may be incorporated into the crown 132, without limitation. For example, in the embodiment illustrated in FIG. 6, two teeth 256 are disposed on the lower surface of the crown 132. The teeth 256 are biased toward a centerline of the crown 132 so as to engage with bone and prevent lateral movement of the crown 132 along the surface of the bone. In another example, FIG. 7 illustrates an embodiment of a surgical staple 260 comprised of a crown 264 that includes an upper reinforced portion 268 and a valley 272 underneath the reinforced portion. In the illustrated embodiment, the valley 272 is centrally disposed along the lower surface of the crown 264 and bordered by edges 276. As will be appreciated, the edges 276 are configured to engage with bone and prevent lateral movement of the crown 264 along the surface of the bone once the surgical staple 260 is implanted. The reinforced portion 268 imparts structural integrity to the surgical staple 260 in compensation for the presence of the valley 264.

Figure 7A:
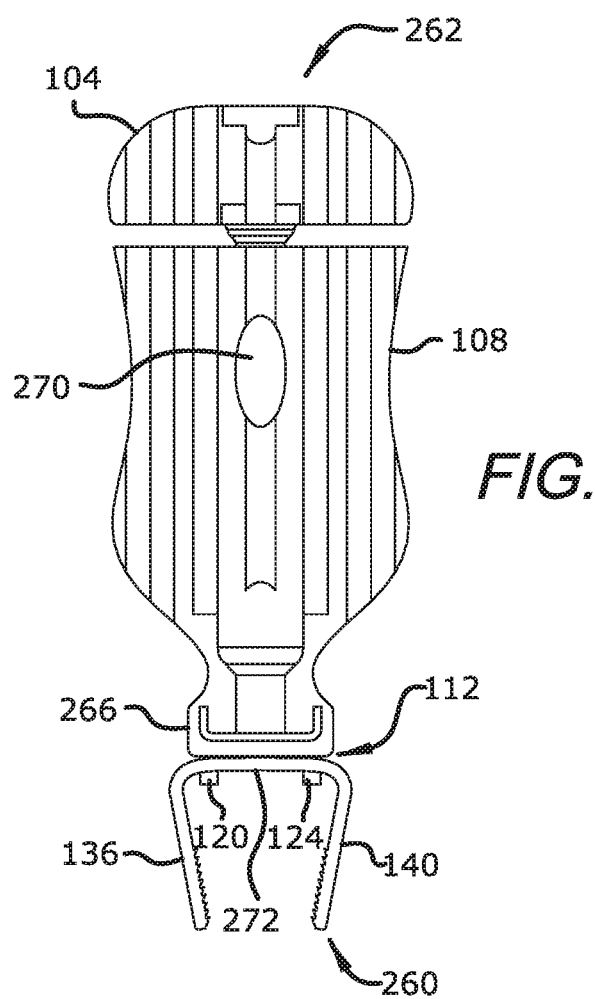
FIG. 7A illustrates a front plan view of the surgical staple of FIG. 7 loaded within a distal force applicator of an exemplary embodiment of a surgical bending instrument that may be used to implant the staple in a patients bone.
Figure 7B:
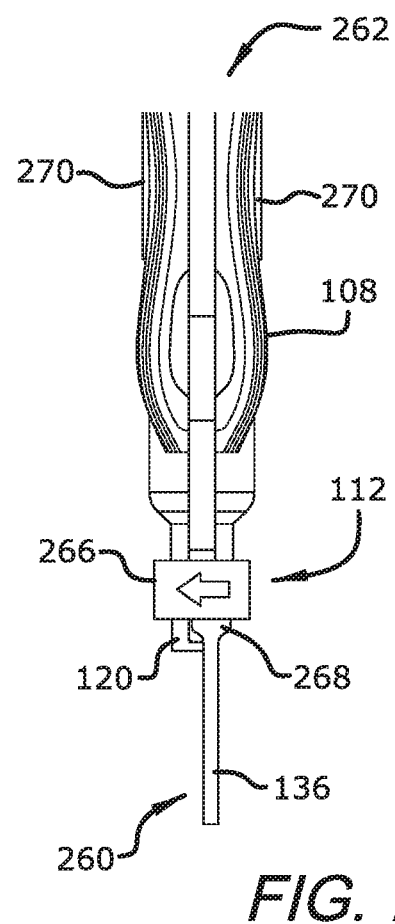
FIG. 7B illustrates a side plan view of the surgical staple of FIG. 7 loaded within the distal force applicator of the surgical bending instrument illustrated in FIG. 7A.

FIGS. 7A-7B illustrate the surgical staple 260 loaded within a distal force applicator 112 of an exemplary embodiment of a surgical bending instrument 262 that may be used to implant the staple in a patient's bone, as described herein. Similar to the surgical bending instrument 100, discussed with respect to FIG. 1, the surgical bending instrument 262 comprises a proximal handle 104, a body 108, as well as the distal force applicator 112. As best shown in FIG. 7A, the distal force applicator 112 comprises a first grip 120 and a second grip 124. A driver 128 (not shown in FIG. 7A) is centered between the first and second grips 120, 124, as disclosed hereinabove. The first and second grips 120, 124 are configured to cooperate so as to support the crown 264 of the surgical staple 260 when the driver 128 is placed into forcible contact with the center of the upper reinforced portion 268 of the crown 264. The first and second grips 120, 124 contact opposite ends of an underside of the crown 264 with the valley 272 therebetween. The forces on the crown 264 due to the driver 128 and the grips 120, 124 operate to retain the surgical staple 260 within the distal force applicator 112, thereby facilitating implanting the staple into the patient. As shown in FIG. 7A, the first and second grips 120, 124 engage the surgical staple 260 on the same side of the crown 264. A direction indicator 266 disposed near the distal force applicator 112 is configured to inform a practitioner of a preferred direction to insert the surgical staple 260 into the distal force applicator so as to engage the crown 264 with the first and second grips 120, 124. The direction indicator 266 may be embossed, engraved, printed, or otherwise disposed on the surgical bending instrument 262 so as to be directly visible to the practitioner.

The first and second grips 120, 124 may have a separation distance comparable with the length of the crown 264. Thus, as illustrated in FIGS. 7A-7B, the first grip 120 may be positioned between the first leg 136 and the edge 276 of the valley 272, and the second grip 124 may be positioned between the second leg 140 and the edge 276 of the valley 272. It will be appreciated, therefore, that the distal force applicator 112 of the surgical bending instrument 262 may be used with a variety of differently-sized surgical staples 260 so long as the valley 272 may be disposed between the grips 120, 124. As such, in some embodiments, the surgical bending instrument 262 may include a size indicator 270 that informs the practitioner of an overall size, or a group of sizes, of the surgical staple 260 that may be implanted into bone by way of the surgical bending instrument 262. It is contemplated, that the size indicator 270 may be embossed, engraved, printed, or otherwise disposed on the surgical bending instrument 262 so as to be directly visible to the practitioner.

Figure 8:
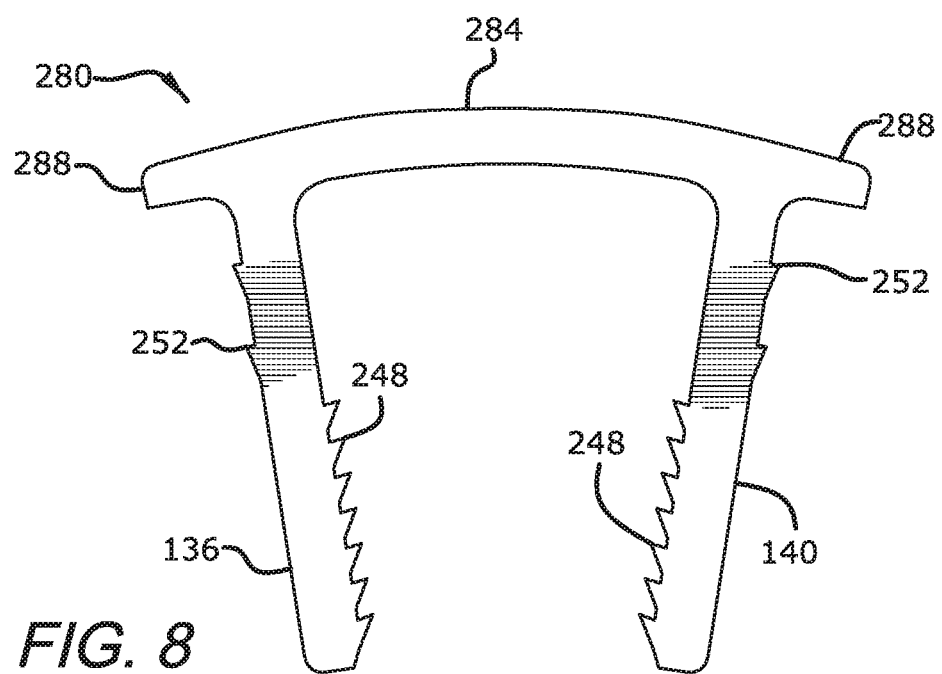
FIG. 8 illustrates a side plan view of an exemplary embodiment of a surgical staple that is indicated for fixation of osteotomies and joint arthrodeses of the hands and feet.

FIG. 8 illustrates a side plan view of an exemplary embodiment of a surgical staple 280 that is indicated for fixation of osteotomies and joint arthrodeses of the hands and feet. The surgical staple 280 is similar to the surgical staple 244, illustrated in FIG. 6, and thus the surgical staple 280 is comprised of a first leg 136 and a second leg 240 that both include inner teeth 248 and exterior teeth 252, as described hereinabove. Unlike the surgical staple 244, however, the surgical staple 280 is comprised of a crown 284 that is includes a wing portion 288 that extends beyond each of the legs 136, 140. Disposed at opposite ends of the crown 284, the wing portions 288 cooperate with the teeth 248, 252, as well as with the center portion of the crown 284, to fixate the surgical staple 280 once implanted in bone.

It should be understood that the wing portions 288 are not to be limited to being incorporated into the illustrated embodiment of the surgical staple 280, shown in FIG. 8, but rather the wing portions 288 may be practiced in combination with any of various features disclosed in connection with the surgical staples 244, 260. For example, in some embodiments, the wing portions 288 may be incorporated into the crown 132 comprising the surgical staple 244. Thus, the wing portions 288 and the teeth 252 may cooperate to fixate the surgical staple 244 once implanted into bone. Further, in some embodiments, the wing portions 288 may be combined with the upper reinforced portion 268 and the valley 272 to fixate the surgical staple 260 implanted in bone. It is further contemplated, therefore, that in some embodiments, the wing portions 288 may be practiced in absence of all of the teeth 248, 252, the reinforced portion 268, and the valley 272, without limitation.

Figure 8A:
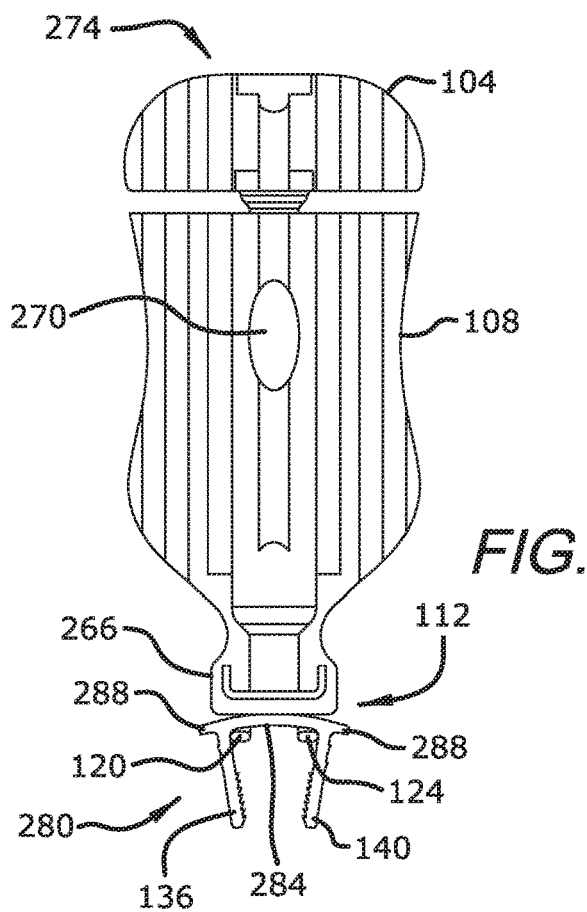
FIG. 8A illustrates a front plan view of the surgical staple of FIG. 8 loaded into the distal force applicator of an exemplary embodiment of a surgical bending instrument that may be used to implant the staple in a patient's bone.

As will be appreciated, the surgical staple 280 may be implanted into a patient's bone by way of a surgical bending instrument, as described herein. For example, FIG. 8A illustrates a front plan view of the surgical staple 280 loaded into the distal force applicator 112 of an exemplary embodiment of a surgical bending instrument 274. As will be recognized, the surgical bending instrument 274 is substantially the same as the surgical bending instrument 262, illustrated in FIGS. 7A-7B, with the exception that the surgical bending instrument 274 is configured for implanting differently-sized staples than the surgical bending instrument 262 of FIGS. 7A-7B. As such, the size indicator 270 disposed on the surgical bending instrument 274 indicates the sizes of the surgical staple 280 that may be implanted by way of the surgical bending instrument 274.

Figure 8B:
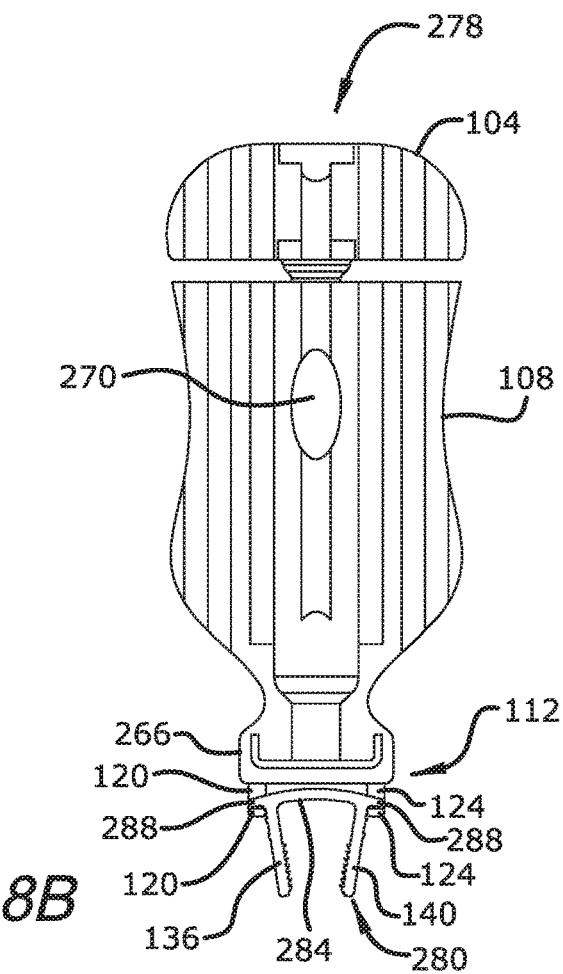
FIG. 8B illustrates a front plan view of the surgical staple of FIG. 8 loaded into an exemplary embodiment of a surgical bending instrument that engages the staple by way of wing portions comprising the surgical staple.

In the embodiment illustrated in FIG. 8A, the surgical staple 280 is loaded into the distal force applicator 112 of the surgical bending instrument 274 such that the first and second grips 120, 124 are engaged with the crown 284 between the first leg 136 and the second leg 140. In some embodiments, however, the wing portions 288 may be received by the first and second grips 120, 124 for the purpose of distracting the staple as disclosed herein. For example, FIG. 8B illustrates a front plan view of the surgical staple 280 loaded into an exemplary embodiment of a surgical bending instrument 278 that engages the staple by way of the wing portions 288. The first and second grips 120, 124 cooperate to support the wing portions 288 of the crown 284 when the driver 128 is placed into forcible contact with the center of the crown 284. The force on the crown 284 due to the driver 128 and the force on the wing portions 288 due to the grips 120, 124 operate to retain the surgical staple 280 within the distal force applicator 112, and thus facilitate implanting the staple into the patient. As will be appreciated, engaging the wing portions 288 on opposite ends of the crown 284 advantageously prevents the surgical staple 280 from becoming dislodged from the distal forced applicator 112 during distracting the staple or implantation into the patient.

Figure 9:
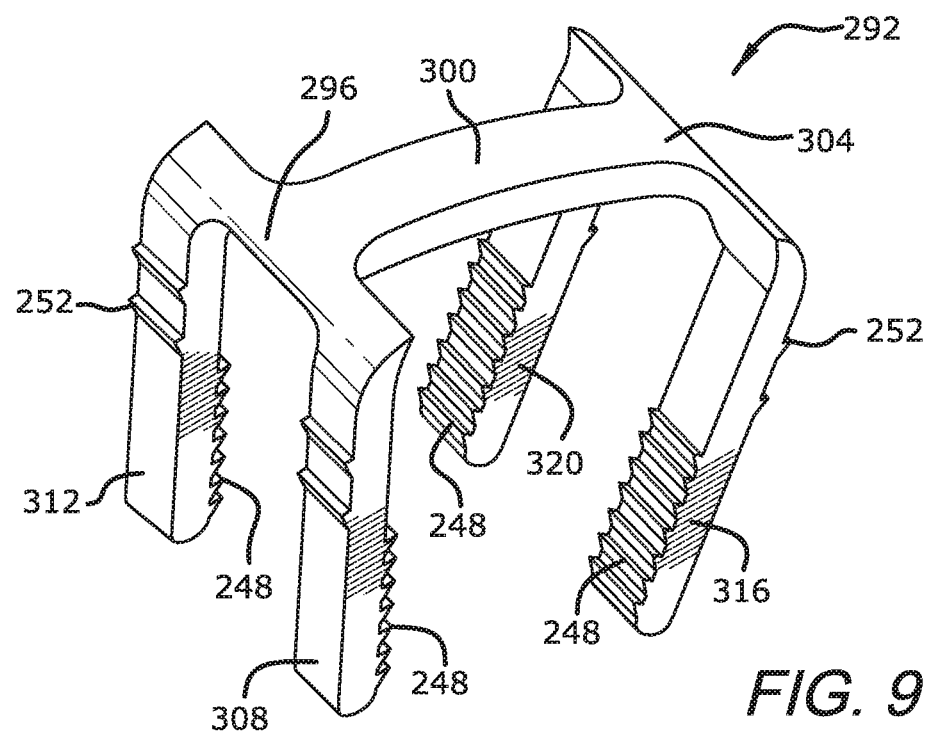
FIG. 9 illustrates an upper perspective view of an exemplary embodiment of a surgical staple that may be implanted into bone in accordance with the present disclosure.

FIG. 9 illustrates an upper perspective view of an exemplary embodiment of a surgical staple 292 that may be implanted into bone in accordance with the present disclosure. The surgical staple 292 generally is indicated for fixation of osteotomies and joint arthrodeses of the hands and feet. In some embodiments, the surgical staple 292 may be comprised of a material that is amenable to being placed into the distracted configuration and relaxed therefrom, such as by way of any of the surgical bending instruments 100, 160, 196. Similar to the surgical staples discussed with respect to FIGS. 2-8, the surgical staple 292 may be comprised of a metal alloy that exhibits shape memory and superelastic properties, such as Nitinol or other similar material.

As will be appreciated, the surgical staple 292 is similar to the surgical staple 244, illustrated in FIG. 6, with the exception that the surgical staple 292 is comprised of four legs in lieu of solely the first and second legs 136, 140 comprising the surgical staple 244. As shown in FIG. 9, the surgical staple 292 is comprised of a first transverse portion 296 disposed at one end of a crown 300 and a second transverse portion 304 disposed at an opposite end of the crown 300. A first leg 308 and a second leg 312 extend downward and parallelly from opposite ends of the first transverse portion 296. Similarly, a third leg 316 and a fourth leg 320 extend downward and parallelly from opposing ends of the second transverse portion 304. The first and second legs 308, 312 angle respectively toward the third and fourth legs 316, 320, giving the surgical staple 292 a resemblance of two of the surgical staples 244 coupled together in parallel. Thus, the first leg 308 and the third leg 316 cooperate similarly to the legs 136, 140 of a first surgical staple 244, and the second leg 312 and the fourth leg 320 cooperate similarly to the legs 136, 140 of a second surgical staple 244. As such, the surgical staple 292 is particularly well suited for implantation into four holes that are drilled in bone across a bone fusion site.

Figure 9A:
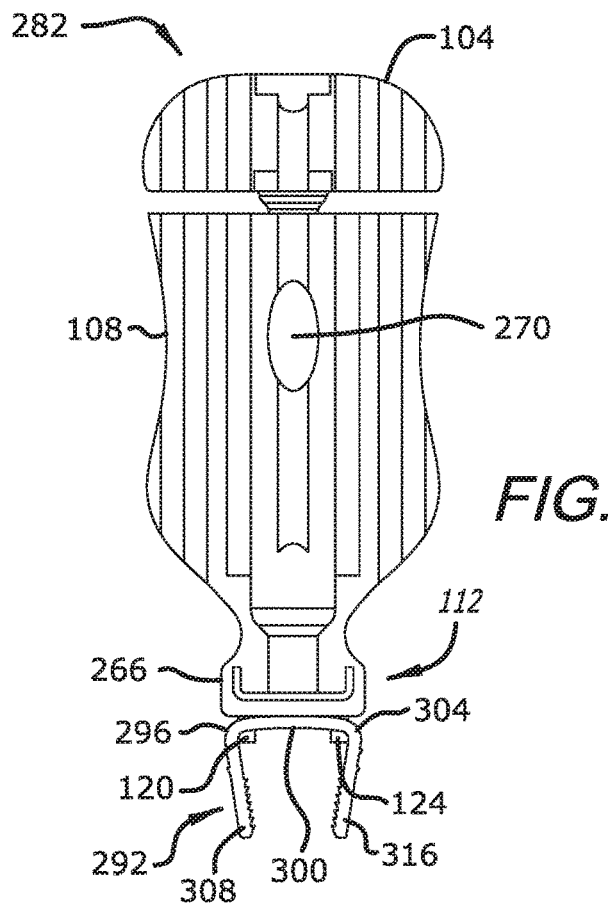
FIG. 9A illustrates a front plan view of the surgical staple of FIG. 9 engaged with an exemplary embodiment of a surgical bending instrument that may be used to implant the staple in a patient's bone.
Figure 9B:
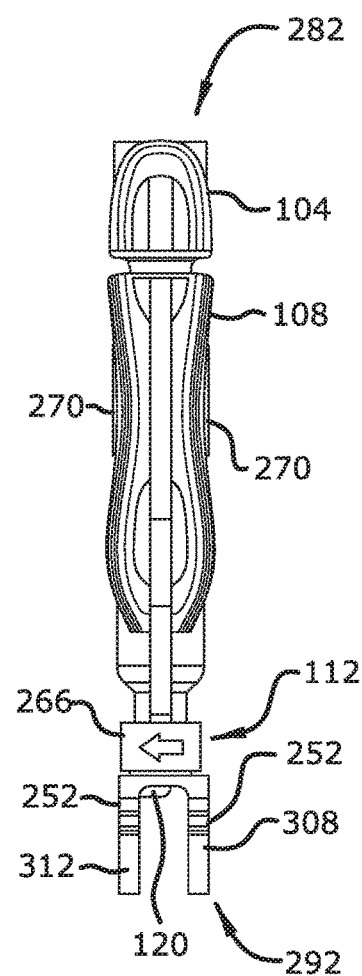
FIG. 9B illustrates a side plan view of the surgical staple of FIG. 9 engaged with the exemplary embodiment of the surgical bending instrument shown in FIG. 9A.

It is contemplated that although the surgical staple 292 is comprised of four legs, the surgical staple may be advantageously implanted into a patient's bone by way of a suitable surgical bending instrument. As such, FIGS. 9A-9B illustrate the surgical staple 292 engaged with an exemplary embodiment of a surgical bending instrument 282, according to the present disclosure. The surgical bending instrument 282 is substantially identical to the surgical bending instrument 262, illustrated in FIGS. 7A-7B, with the exception that the surgical bending instrument 282 is configured for implanting differently-sized staples than the surgical bending instrument 262 of FIGS. 7A-7B. Similar to the surgical bending instrument 262, the surgical bending instrument 282 includes a size indicator 270 that indicates the sizes of the surgical staple 292 that may be implanted by way of the surgical bending instrument 282. The size indicator 270 may be embossed, engraved, printed, or otherwise disposed on the surgical bending instrument 282 so as to be directly visible to the practitioner.

As shown in FIGS. 9A-9B, the first and second grips 120, 124 comprising the surgical bending instrument 282 are configured to cooperatively support the crown 300 of the surgical staple 292 when the driver 128 (not shown) is placed into forcible contact with the center of the crown 300. The first and second grips 120, 124 contact opposite ends of the underside of the crown 300 with the first and second transverse portions 296, 304 respectively disposed outside the grips 120, 124. Further, the first and second grips 120, 124 engage the surgical staple 292 on the same side of the crown 300. As disclosed herein, a direction indicator 266 may be disposed near the distal force applicator 112 and configured to inform the practitioner of a preferred direction to insert the surgical staple 292 into the distal force applicator so as to engage the crown 300 with the first and second grips 120, 124.

The first and second grips 120, 124 may have a separation distance comparable with the length of the crown 300. Thus, the first grip 120 may engage the end of the crown 300 abutting the first transverse portion 296, and the second grip 124 may engage the end of the crown 300 abutting the second transverse portion 304. It should be recognized, however, that symmetry of the surgical staple 292 ensures that the first grip 120 may be equivalently engaged with the end of the crown 300 that abuts the second transverse portion 304, and the second grip 124 may be engaged with the end of the crown 300 that abuts the first transverse portion 296. Further, it should be understood that the surgical bending instrument 282 may be used with a variety of differently sized surgical staples 292 so long as opposite ends of the crown 300 may be suitably engaged with the grips 120, 124. To this end, the size indicator 270 preferably is configured to indicate the overall size, or group of sizes, of the surgical staple 292 that may be advantageously implanted by way of the surgical bending instrument 282.

It is contemplated that any of the legs 308, 312, 316, 320 may be practiced in combination with any of the various features disclosed hereinabove in connection with the surgical staples 244, 260, 280, without limitation. For example, in the illustrated embodiment of FIG. 9, each of the legs 308, 312, 316, 320 includes multiple inner teeth 248 and a pair of exterior teeth 252, as described herein. The teeth 248 disposed on the first and second legs 308, 312 are oriented toward the teeth 248 disposed on the third and fourth legs 316, 320. Thus, once the surgical staple 292 is implanted into bone and allowed to relax from the distracted configuration, the legs 308, 312, 316, 320 cooperatively compress the bones to be fused as the staple attempts to return to the initial configuration illustrated in FIG. 9. The teeth 248 engage with the bone and ensure that the implanted surgical staple 292 remains fixated. The exterior teeth 252 operate similarly to the teeth 248, engaging with the bone and fixating the surgical staple 292, as disclosed herein.

It is contemplated that the surgical staple 292 may be practiced in combination with any of various features disclosed in connection with the surgical staples 244, 260, 280, without limitation. For example, in some embodiments, the wing portions 288 may be incorporated into the crown 300. In some embodiments, wing portions 288 may be coupled with the opposite ends of each of the first and second transverse portions 296, 304. It is envisioned, therefore, that the wing portions 288 may cooperate with the teeth 248, 252 to fixate the surgical staple 292 once implanted into bone. Further, in some embodiments, the wing portions 288 may be incorporated into the crown 300 in combination with the upper reinforced portion 268 and the valley 272 to fixate the surgical staple 260 implanted in bone. Moreover, in some embodiments, the wing portions 288 may be incorporated into the surgical staple 292 in lieu of any or all of the teeth 248, 252, the reinforced portion 268, and the valley 272, without limitation.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A surgical bending instrument for implanting a surgical staple at a bone fusion site of a patient, comprising:
    a body supporting a first grip and a second grip that are configured to retain a crown of the surgical staple;
    a driver configured to exert a distally-directed force onto a top of the crown between the first grip and the second grip; and
    a proximal handle configured to move the driver longitudinally relative to the body;
    wherein the proximal handle comprises a lever coupled with a cam that is pivotally mounted within the body, such that proximal movement of the lever causes the cam to push the driver into forcible contact with the crown.

2. The surgical bending instrument of claim 1, wherein the first grip and the second grip are disposed on the same side of the surgical staple and configured to support, opposite ends underneath the crown.

3. The surgical bending instrument of claim 1, wherein the first grip and the second grip are configured to forcibly retain the crown when the driver contacts a center of the crown.

4. The surgical bending instrument of claim 1, wherein the first grip and the second grip have a separation distance comparable with a length of the crown.

5. The surgical bending instrument of claim 4, wherein the first grip and the second grip have an adjustable separation distance so as to facilitate retaining a variety of differently-sized surgical staples.

6. The surgical bending instrument of claim 1, wherein moving the lever to a maximally proximal position places the surgical staple into a distracted configuration suitable for implantation across the bone fusion site.

7. The surgical bending instrument of claim 6, wherein moving the lever distally allows the surgical staple to relax from the distracted configuration and compress the bone fusion site.

8. A surgical bending instrument for distracting a surgical staple for implantation at a bone fusion site of a patient, comprising:
    a first grip and a second grip that are disposed on the same side of the surgical staple and configured to support opposite ends underneath a crown of the surgical staple;
    a driver in mechanical communication with a proximal handle and configured to exert a distal force on top of the crown; and
    a body supporting at least the first grip, the second grip, and the driver;
    wherein the proximal handle is coupled with the driver by way of a cam that is mounted pivotally within the body, whereby moving a lever coupled with the cam moves the driver longitudinally relative to the body.

9. The surgical bending instrument of claim 8, wherein the proximal handle is configured to facilitate moving the driver distally to clasp the crown between the first grip, the second grip, and the driver, and thereby place the surgical staple into a distracted configuration suitable for implantation across the bone fusion site, and wherein the proximal handle is configured to move the driver proximally to allow the surgical staple to relax from the distracted configuration and compress the bone fusion site after implantation.

* * * * *